(12) United States Patent
Merz et al.

(10) Patent No.: US 8,864,968 B2
(45) Date of Patent: Oct. 21, 2014

(54) ELECTROCHEMICAL SENSOR

(75) Inventors: Matthias Merz, Leuven (BE); Youri Victorovitch Ponomarev, Leuven (BE)

(73) Assignee: NXP B.V., Eindhoven (NL)

( * ) Notice: Subject to any disclaimer, the term of this patent is extended or adjusted under 35 U.S.C. 154(b) by 816 days.

(21) Appl. No.: 12/858,353

(22) Filed: Aug. 17, 2010

(65) Prior Publication Data

US 2011/0036913 A1    Feb. 17, 2011

(30) Foreign Application Priority Data

Aug. 17, 2009  (EP) .................................... 09252002

(51) Int. Cl.
| | | |
|---|---|---|
| G01N 27/333 | (2006.01) | |
| G01N 27/416 | (2006.01) | |
| G01N 27/414 | (2006.01) | |

(52) U.S. Cl.
CPC .......... *G01N 27/333* (2013.01); *G01N 27/4167* (2013.01); *G01N 27/414* (2013.01)
USPC ........... 204/433; 204/435; 204/414; 204/416; 257/253

(58) Field of Classification Search
CPC  G01N 27/4167; G01N 27/333; G01N 27/414
USPC ................... 257/253; 204/435, 414, 416, 433
See application file for complete search history.

(56) References Cited

U.S. PATENT DOCUMENTS

| | | | |
|---|---|---|---|
| 4,940,945 A | | 7/1990 | LittleJohn et al. |
| 5,238,553 A | * | 8/1993 | Hettiarachchi et al. ....... 204/435 |
| 5,250,168 A | * | 10/1993 | Tsukada et al. ............... 204/416 |
| 5,336,388 A | * | 8/1994 | Leader et al. ............ 204/403.06 |
| 5,342,498 A | | 8/1994 | Graves et al. |
| 5,376,255 A | * | 12/1994 | Gumbrecht et al. .......... 204/426 |
| 5,841,021 A | * | 11/1998 | De Castro et al. ............. 73/23.2 |
| 5,844,200 A | * | 12/1998 | Leader et al. ............. 219/121.71 |
| 6,663,756 B2 | * | 12/2003 | Lee et al. ....................... 204/415 |
| 2002/0027074 A1 | * | 3/2002 | Tominaga et al. ............. 204/414 |
| 2003/0209451 A1 | * | 11/2003 | Dineen et al. ................. 205/789 |
| 2006/0025748 A1 | * | 2/2006 | Ye .................................. 604/503 |
| 2006/0159590 A1 | * | 7/2006 | Pechstein et al. ............... 422/88 |
| 2006/0226985 A1 | * | 10/2006 | Goodnow et al. .......... 340/572.1 |
| 2007/0003209 A1 | | 1/2007 | Papautsky et al. |
| 2009/0294284 A1 | * | 12/2009 | Hsiung et al. ............. 204/290.05 |

FOREIGN PATENT DOCUMENTS

| | | | |
|---|---|---|---|
| WO | 2006/086423 A | | 8/2006 |
| WO | WO2010/001277 | * | 1/2010 |

OTHER PUBLICATIONS

Shin et al. (Anal. Chem. 2000, 72, 4468-4473).*
Shimada et al. (Med. & Biol. Eng, & Comput., 1980, 18, 741-745).*
Margules et al., J. 8iomed. Eng. 1987, vol. 9, January, pp. 21-25.*
A. Simonis et, al. : 'New Concepts of Miniaturised Reference Electrodes in Silicon Technology for Potentiometric Sensor System,' Sensors and Actuators B, Elsevier Sequoia S.A., vol. 103, No. 1-2, pp. 429-435 (Sep. 29, 2004).
A Simonis, et al. : 'Miniaturised Reference Electrodes for Field-Effect Sensors Compatible to Silicon Chip Technology,' Electrochemica Acta, vol. 51, pp. 930-937, (Aug. 9, 2005).
European Extended Search Report for Patent Appln. No. EP09252002.2 (Jan. 2010).

* cited by examiner

*Primary Examiner* — Jennifer Dieterle

(57) ABSTRACT

An electrochemical sensor device including a sensor chip having an integrated electrochemical sensor element; and a substrate having a first surface on which the sensor chip is mounted, the substrate comprising a reference electrode structure for the integrated electrochemical sensor element, the reference electrode structure connected to the sensor chip via an electrical connection on the first surface of the substrate.

15 Claims, 2 Drawing Sheets

US 8,864,968 B2

ELECTROCHEMICAL SENSOR

This application claims priority to EPO Patent Application No. 09252002.2 filed Aug. 17, 2009, the entire disclosure of which is herein expressly incorporated by reference.

FIELD OF THE INVENTION

The invention relates to a miniature electrochemical sensor such as pH sensor, for example comprised in an RFID tag having a pH sensing capability.

BACKGROUND OF THE INVENTION

Over 600 million RFID (radio frequency identification) tags are estimated to have been delivered in 2005. Applications of such devices range from identification and access control to counterfeit prevention and logistics. Such tags may be either active or passive, active RFID tags being powered by a permanent power supply (for example provided by a battery) while passive RFID tags are powered via an RF link and therefore only operate when in communication with a reader. Supply chain monitoring is a large market for active tags equipped with a sensor and a memory for storing measured data. For example, active tags having a temperature sensor can be configured to record the actual temperature of frozen food or other goods that need to be cooled or maintained within a preferred temperature range. Depending on the allowed 'thermal budget', i.e. an indication of the integrated temperature during storage and transport, the shelf-life of an associated product can be calculated on an individual or batch basis. Moreover, such active tags can indicate if certain limits such as a maximum or minimum temperature have been reached and, if so, whether the product must be discarded. Besides temperature, other parameters such as pH and gas composition, which may also be used for determining the lifetime of a product, could usefully be incorporated into such sensors. Problems related to measuring such other parameters, however, include those of integration and miniaturisation.

Electrochemical sensors, such as pH sensors based on the ISFET (Ion-Selective Field Effect Transistor) principle, require a reference electrode to define the potential of the analyte. The reference electrode maintains the analyte (electrolyte) potential at a fixed value irrespective of the analyte composition. The reference electrode is therefore an essential component of a pH sensor.

A standard reference electrode is, by definition, based on a hydrogen electrode, composed of a platinized (i.e. platinum black coated) platinum sheet immersed in an acid electrolyte solution through which hydrogen gas is bubbled. This standard electrode is clearly not practical for large scale commercial use or for miniaturisation. More practical types of standard electrodes such as those based on Ag/AgCl reference electrodes are frequently used instead. An Ag/AgCl based reference electrode structure typically comprises a chlorinated silver wire (Ag/AgCl) in contact with a well defined reference electrolyte, such as an aqueous KCl solution (typically 3M KCl). Galvanic contact to the analyte is generally established via a diaphragm, which may be in the form of a porous frit made from an inert material such as a glass or ceramic. During operation, the electrolyte must continuously flow out of the reference electrode into the analyte. Other types of reference electrodes include those based on mercury and mercury chloride (also known as a calomel) or thallium and thallium chloride Tl/TlCl electrodes may be used for specific applications such as elevated temperatures. The general principle is, however, the same as for an Ag/AgCl electrode, in particular through the use of liquid reference electrolyte and contact via a diaphragm.

When considering the use of reference electrodes for miniature pH sensors, there are several disadvantages of the above standard types of reference electrodes, including a large form factor, requiring at least several cubic mm to provide sufficient volume for the reference electrode structure, relatively high cost, and the need for the electrolyte to be refilled at regular intervals. These disadvantages make the use of standard reference electrodes for miniaturized chemical sensors, for example for integration into RFID tags, difficult or impossible. Depletion of the reference electrolyte is, however, a relatively minor issue for sensors with RFID applications due to their limited service life.

A. Simonis et al., in *Electrochimica Acta* 51(2005) 930-937 disclose a planar reference electrode structure having a gel-based reference electrolyte formed on a silicon substrate attached to a PCB (printed circuit board). An Ag/AgCl layer is formed on an oxidised surface of the silicon substrate, and a gel electrolyte of either agar or pHEMA (poly-(2-hydroxyethyl methacrylate)) with KCl provides a defined ion concentration at the interface to the Ag/AgCl electrode, in a similar way to a 3M KCl solution used in conventional reference electrodes. A diffusion barrier layer of PVC and nafion or of cellulose nitrate is provided on the gel electrolyte to limit out-diffusion of KCl from the electrolyte, in order to increase the lifetime of the device. If too much KCl is removed from the gel the KCl concentration at the Ag/AgCl electrode interface changes, causing the reference potential to change. The maximum service life is then reached, as pH measurements are then inaccurate. The diffusion barrier also mechanically protects the underlying gel electrolyte.

The type of reference electrode structure described by A. Simonis et al. is intended to be integrated with an ISFET type sensor together with other electronic components such as amplifiers, microcontrollers, memory, RF units etc. A disadvantage of this approach, however, is that the reference electrode structure needs to have a minimum area of at least several mm2, in order to form a low ohmic contact and to maintain a minimum ion reservoir volume for proper operation. If the volume of the gel reservoir is too small, the ions become depleted too quickly and the device will have only a very short service life. Any practical solution, where a service life of the order of hundreds or thousands of hours is required, would typically require far too much chip area to be commercially viable, particularly for use as part of an RFID device, in which the silicon area is generally less than 1 $mm^2$ and the cost of such devices needs to be minimal.

SUMMARY OF THE INVENTION

In accordance with a first aspect of the invention there is provided an electrochemical sensor device comprising:
  a sensor chip having an integrated electrochemical sensor element; and
  a substrate having a first surface on which the sensor chip is mounted, the substrate comprising a reference electrode structure for the integrated electrochemical sensor element, the reference electrode structure connected to the sensor chip via an electrical connection on the first surface of the substrate.

The integrated electrochemical sensor element is preferably a pH sensor element, for example in the form of an ISFET sensor.

The reference electrode structure optionally extends through the substrate between the first surface and a second opposing surface of the substrate, thereby exposing the pH sensor to an environment extending over the second surface of the substrate. This has the advantage of minimising the volume taken up by the reference electrode structure, and also allow the substrate to provide a degree of protection for the reference electrode structure. A portion of the reference electrode structure may also extend beyond the second surface, protruding out of the interposer.

The reference electrode structure preferably comprises a gel-based electrolyte adjacent a reference electrode connected to the electrical connection on the first surface of the substrate. The use of a gel-based electrolyte has the advantage of simplifying manufacture of the sensor device, as a containment chamber for a liquid electrolyte is not required.

The gel-based electrolyte may comprise a conductive gel selected from agar and poly-(2-hydroxyethyl methacrylate), and the reference electrode may be in the form of a Ag/AgCl layer.

The gel-based electrolyte is optionally covered by a diffusion barrier layer. The diffusion barrier acts to reduce out-diffusion of ions from the electrolyte as well as to provide a degree of mechanical protection of the fragile gel electrolyte layer.

The electrochemical sensor element is optionally disposed over a hole in the substrate for exposing the electrochemical sensor element to an environment extending over the second surface of the substrate. This configuration allows the substrate to provide protection for the electrochemical sensor element on the chip.

The electrolyte of the reference electrode structure may also be exposed to the environment extending over the second surface of the substrate. This arrangement ensures that the reference electrode structure is exposed in close proximity to the same environment to which the electrochemical sensor element is exposed, ensuring an accurate measurement.

The sensor device may be incorporated into an RFID tag comprising an antenna element electrically connected to an RFID element of the sensor chip via further electrical connections on the first surface of the substrate.

An advantage of the invention is that, by integrating the reference electrode structure into the substrate rather than with the sensor chip, the area of silicon required for the sensor chip is minimised. When incorporating the sensor device into an RFID tag, the substrate is preferably in the form of an interposer or strap configured to provide electrical connections between the sensor chip and an antenna in the RFID package. Using the interposer for both purposes therefore saves on the number of individual components needed to make up the device.

In accordance with a second aspect of the invention there is provided a method of manufacturing an electrochemical sensor device, the method comprising:

providing a substrate having a first surface and a second opposing surface;
applying electrical connections to the first surface of the substrate;
forming a reference electrode structure in the substrate; and
connecting a sensor chip having an integrated electrochemical sensor element to the first surface, electrically connecting the sensor element to the reference electrode structure via the electrical connection.

A hole may be provided in the substrate through which the reference electrode structure is formed, so that the references electrode structure extends through the substrate between the first and second surfaces of the substrate. The hole may be provided either before or after applying the electrical connections to the first surface.

The step of forming the reference electrode structure may include the steps of applying a reference electrode layer over the electrical connection and a gel-based electrolyte layer over the reference electrode. An additional barrier layer may also be applied to cover and protect the gel-based electrolyte.

The sensor chip may be connected such that the electrochemical sensor element in the chip is disposed over a hole in the substrate for exposing the electrochemical sensor element to an environment extending over the second surface of the substrate.

The method of the second aspect of the invention may further include forming an RFID tag comprising the sensor device by electrically connecting an antenna element to an RFID element of the sensor chip via further electrical connections applied on the first surface of the substrate.

BRIEF DESCRIPTION OF THE DRAWINGS

Embodiments of the invention are described below by way of example and with reference to the appended drawings, in which.

DETAILED DESCRIPTION OF THE EMBODIMENTS

An interposer or strap is a small thin plastic substrate having metal contacts and connections. A common size for such a substrate is 5 mm×9 mm. The interposer acts as connector between a semiconductor chip die and an antenna. Since RFID chip dies are very small, high precision is needed for the alignment of electrical contacts on the die to the antenna contacts. This requires complex alignment procedures together with accurate and small antenna structures, which may not be acceptable for ultra low cost RFID applications. The interposer effectively increases the size of the contacts, thereby allowing connections to larger/coarser (and therefore cheaper) antennas. Besides the electrical contacts and traces, no other structures are generally present on a conventional interposer, which potentially allows for the interposer to fulfil other functions. Some of the 'spare' area on the interposer could therefore be used to integrate a reference electrode structure for an electrochemical sensor provided on the RFID chip, as described in more detail below.

Figure 1A:
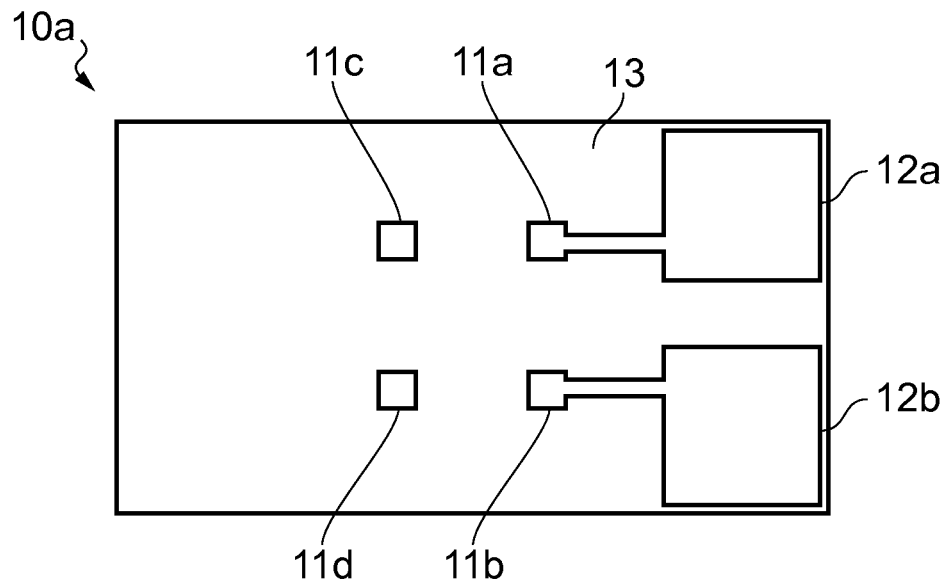
FIG. 1a is a plan view of an interposer substrate for an RFID tag.

FIG. 1a illustrates in plan view a conventional interposer 10a, having die contacts 11a-d and extension contacts 12a, 12b on a first surface 13 of the interposer. The larger extension contacts 12a, 12b connect to an antenna structure (not shown), which allows the RFID chip connected to the smaller contacts 11a-d to communicate wirelessly with remote devices.

Figure 1B:
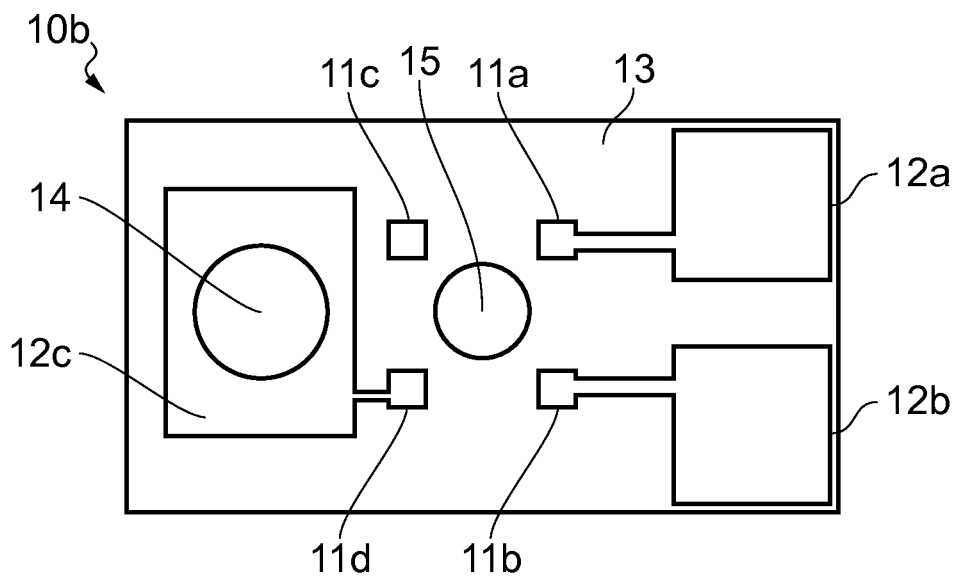
FIG. 1b is a plan view of an interposer substrate for an RFID tag incorporating a reference electrode structure.

FIG. 1b illustrates in plan view a modified interposer 10b, having an additional contact 12c for an electrical connection to a reference electrode structure 14, described in more detail below. In addition, a hole 15 is provided in the interposer 10b, the function of which is described below.

Figure 2A:
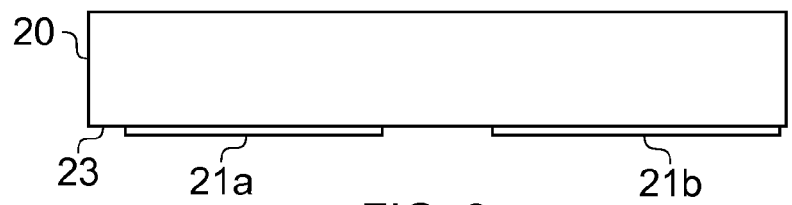
FIGS. 2a to 2f are schematic cross-sectional views of a manufacturing process for a reference electrode structure on an interposer substrate.
Figure 2B:
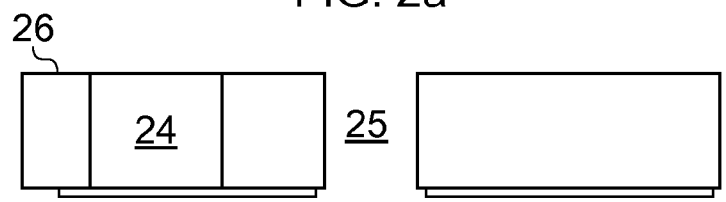

FIGS. 2a to 2f outline a sequence of steps for the manufacture of an integrated reference electrode structure into an interposer. A starting point is a conventional type of interposer substrate 20, on which are provided patterned metal structures for electrical contacts 21a, 21b on a first surface 23, as shown in FIG. 2a. As shown in FIG. 2b, two openings 24, 25 extending through the interposer 20 are made, for example by laser drilling from a second opposing face 26 of the substrate. The opening 24 over the electrical contact 21a stops short of extending through the electrical contact 21a, allowing for an electrical connection to a reference electrode material deposited on the contact 21a. As an alternative to laser drilling through the substrate, the holes 24, 25 could instead be provided by first punching the substrate, followed by application of the metal contacts 21a, 21b on the first surface 23, for example by deposition of a pre-patterned foil using a roll-to-roll process. The processes shown in FIGS. 2a and 2b could therefore be carried out in a different order than indicated.

Figure 2C:
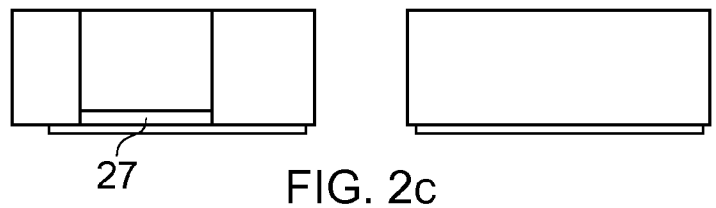

As shown in FIG. 2c, a reference electrode 27 is then deposited onto the back side of the electrical contact 21a, for example by depositing a Ag/AgCl loaded ink through ink jet printing or by screen printing. An optional cleaning step, for example using acids or plasma treatment, may be included prior to deposition of the reference electrode material, in order to remove oxides or other detritus from previous processes such as laser drilling, and to improve contact between the deposited Ag/AgCl and the underlying metal surface.

Figure 2D:
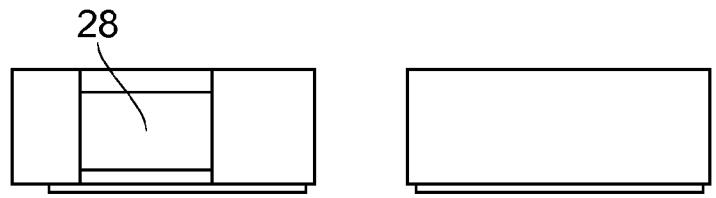

As shown in FIG. 2d, a KCl ion reservoir 28 is then deposited, for example by ink jet or screen printing. Possible compositions for the ion reservoir 28 include agar gel with KCl, pHEMA with KCl, other conductive gels with KCl, or other solid state electrolytes containing KCl.

Figure 2E:
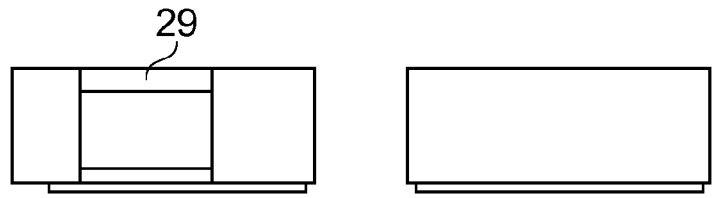

As an optional step, illustrated in FIG. 2e, a barrier layer 29 may be deposited over the ion reservoir 28, in order to reduce out-diffusion of KCl from the reservoir 28, thereby increasing the lifetime of the reference electrode structure. The barrier layer 29 may also serve as mechanical protection for the ion reservoir. Several materials or combinations of materials may be used for the barrier layer 29 to provide a sufficient (but not excessively high) ion conductivity and sufficient mechanical stability. Exemplary materials include PVC, nafion or cellulose nitrate, and combinations thereof Deposition techniques for the barrier layer 29 may again include ink jet printing or screen printing. Alternatively or additionally, a diffusion barrier foil may be laminated over the ion reservoir 28 (not shown). The diffusion barrier layer 29 may also partially extend over the second surface 26 of the substrate 20, resulting in a portion of the reference electrode structure protruding beyond the second surface 26.

Figure 2F:
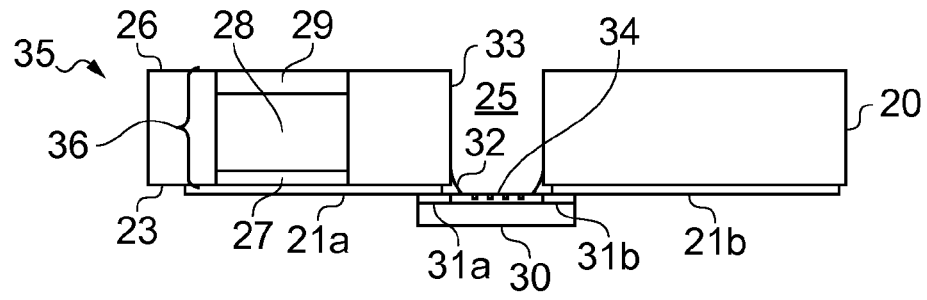

The final form of the electrochemical sensor device 35 having a complete reference electrode structure 36 is illustrated schematically in FIG. 2f. Electrical contacts 31a, 31b of a semiconductor die 30 are attached to the electrical contacts 21a, 21b on the first surface 23 of the interposer 20, for example by means of a flip chip process. Special adhesives, known in the art as anisotropic conductive adhesives (also known as anisotropic conductive films or pastes), can be used for this purpose, where the adhesive becomes conductive when squeezed between two opposing surfaces i.e. between the contacts on the die 30 and interposer contacts 21a, 21b. In addition, a sealing compound 32 may be applied to the interface between the die 30 and the inside wall 33 of the liquid access opening 25. The sealing compound 32, which may be provided by the same adhesive used to connect the die 30 to the interposer contacts 21a, 21b, prevents any direct contact between the analyte and the contacts 21a, 21b connecting the die 30 to the interposer 20 which could otherwise cause a short circuit or corrosion. A pH sensor element 34 is provided on the die, facing into the liquid access opening 25 in the interposer substrate for exposing the pH sensor to an environment extending over the second surface of the substrate 20.

The invention is not necessary limited to Ag/AgCl electrodes and KCl electrolyte. Other reference electrodes such as Tl/TlCl, calomel etc. can also be integrated in the same or a similar way. Electrolytes containing other ion compositions could also be used, such as NaCl, CaCl. Generally, the electrolyte must contain the same anion (in the case of Ag/AgCl the ion is Cl) as the low solubility salt (in case of the Ag/AgCl this is AgCl) that contacts the metal electrode (in case of Ag/AgCl this is Ag).

When choosing the type of reference electrode, several aspects must also be taken into account, such as corrosion resistance, and food or biocompatibility. While a Ag/AgCl-based reference electrode structure may be food- and biocompatible, a Hg-based calomel electrode would certainly not be.

An electrochemical sensor device in accordance with the invention may be used as a reference electrode for ultra-low cost chemical sensors. The sensor device may be of particular use in RFID tag applications, where control and monitoring of a supply chain is required, such as for perishable goods where a measure of the pH of the environment would be advantageous. In the case of an RFID sensor, the other electrical connections, one of which 21b is shown in FIG. 2f, are used to connect the chip 30 to an antenna.

Other embodiments are also intended to be within the scope of the invention, which is to be defined by the appended claims.

The invention claimed is:

1. An electrochemical sensor device comprising:
a sensor chip having an integrated electrochemical sensor element; and
a substrate having a first surface on which the sensor chip is mounted and a second surface;
a reference electrode structure including a reference electrode and a gel-based electrolyte adjacent thereto, the reference electrode structure configured and arranged with the integrated electrochemical sensor element for sensing pH, the reference electrode structure connected to the sensor chip via an electrical connection on the first surface of the substrate;
a liquid access opening through the substrate from the first surface of the substrate to the second surface of the substrate and configured and arranged to expose the integrated electrochemical sensor element; and
a diffusion barrier layer covering the gel-based electrolyte and configured and arranged to mitigate out-diffusion of electrolytes from the gel-based electrolyte.

2. The sensor device of claim 1 wherein the electrochemical sensor element is a pH sensor element.

3. The sensor device of claim 1 wherein the reference electrode structure extends through the substrate between the first surface and a second opposing surface of the substrate.

4. The sensor device of claim 1 wherein the gel-based electrolyte adjacent the reference electrode is exposed to an environment extending over a second opposing surface of the substrate, wherein the integrated electrochemical sensor element is exposed to the environment extending over a second surface of the substrate.

5. The sensor device of claim 1 wherein the gel-based electrolyte includes a conductive gel selected from agar and poly-(2-hydroxyethyl methacrylate).

6. The sensor device of claim 1 wherein the reference electrode is in the form of a Ag/AgCl layer.

7. The sensor device of claim 1 wherein the gel-based electrolyte includes a conductive gel or solid state electrolytes, and wherein the diffusion barrier layer is further configured and arranged to increase a lifetime of the reference electrode structure.

8. The sensor device of claim 3 wherein the electrochemical sensor element is disposed over a hole in the substrate for exposing the electrochemical sensor element to an environment extending over the second surface of the substrate.

9. An RFID tag comprising the sensor device of claim 1, the RFID tag comprising an antenna element electrically connected to an RFID element of the sensor chip via further electrical connections on the first surface of the substrate.

10. A method of manufacturing an electrochemical sensor device, the method comprising:
providing a substrate having a first surface and a second opposing surface;
applying electrical connections to the first surface of the substrate;
forming a reference electrode structure in the substrate;
connecting a sensor chip having an integrated electrochemical sensor element to the first surface, electrically connecting the sensor element to the reference electrode structure via the electrical connection;
providing a liquid access opening through the substrate and from the first surface of the substrate to the second surface of the substrate and configured and arranged to expose the integrated electrochemical sensor element;
applying a reference electrode layer over the electrical connection;
applying a gel-based electrolyte layer over the reference electrode layer; and
covering the gel-based electrolyte layer with a diffusion barrier layer.

11. The method of claim 10 wherein a hole is provided in the substrate within which the reference electrode structure is formed, such that the reference electrode structure extends through the substrate between the first and second surfaces of the substrate.

12. The method of claim 10 wherein
applying the gel-based electrolyte layer includes depositing an ion reservoir.

13. The method of claim 12 wherein covering the gel-based electrolyte layer with the diffusion barrier layer includes depositing PVC, nafion, a cellulose material, or a combination thereof.

14. The method of claim 10 wherein the sensor chip is connected such that the integrated electrochemical sensor element in the chip is disposed over a hole in the substrate for exposing the electrochemical sensor to an environment extending over the second surface of the substrate.

15. The method of claim 10 further comprising forming an RFID tag comprising the sensor device by electrically connecting an antenna element to an RFID element of the sensor chip via further electrical connections applied on the first surface of the substrate.

\* \* \* \* \*